United States Patent [19]

Yacowitz

[11] Patent Number: 5,054,339
[45] Date of Patent: Oct. 8, 1991

[54] TATTOOING ASSEMBLY

[76] Inventor: Harold Yacowitz, 221 Second Ave., Piscataway, N.J. 08854

[21] Appl. No.: 630,004

[22] Filed: Dec. 19, 1990

Related U.S. Application Data

[63] Continuation-in-part of Ser. No. 481,944, Feb. 20, 1990.

[51] Int. Cl.$^5$ .......................... B26F 1/24; A61B 17/20
[52] U.S. Cl. ...................................... 81/9.22; 604/47; 606/186
[58] Field of Search ......... 81/9.22; 604/257, 183–186, 604/46, 47; 606/184, 185, 186

[56] References Cited

U.S. PATENT DOCUMENTS

| 304,613 | 9/1884 | Carey | 81/9.22 |
|---|---|---|---|
| 473,207 | 4/1892 | Carey | 81/9.22 |
| 768,413 | 8/1904 | Wagner | 81/9.22 |
| 1,724,812 | 8/1929 | Waters | 81/9.22 |
| 2,437,920 | 5/1948 | Overton | 604/47 |
| 4,671,277 | 6/1987 | Beuchat | 81/9.22 |
| 4,715,853 | 12/1987 | Prindle | 604/257 |
| 4,771,660 | 9/1988 | Yacowitz | 81/9.22 |
| 4,798,582 | 1/1989 | Sarath et al. | 81/9.22 |
| 4,914,988 | 4/1990 | Chang | 81/9.22 |

FOREIGN PATENT DOCUMENTS

| 266682 | 1/1929 | Italy . | |
| 13539 | of 1899 | United Kingdom | 81/9.22 |

Primary Examiner—Roscoe V. Parker
Attorney, Agent, or Firm—Robert A. Green

[57] ABSTRACT

Tattooing apparatus including a vibratable housing carrying a tattooing needle and a source of tattooing pigment coupled by flexible tubing to said needle through a peristaltic pump by which the flow of pigment to the needle is controlled.

8 Claims, 3 Drawing Sheets

TATTOOING ASSEMBLY

CROSS REFERENCE TO RELATED APPLICATIONS

This application is a continuation-in-part of application Ser. No. 07/481,944 filed Feb. 20, 1990.

BACKGROUND OF THE INVENTION

Tattooing is performed by means of a sharp, small diameter needle or cluster of needles which is dipped in a tattooing pigment. The needle, or needle unit, carrying pigment is vibrated into the skin to be tattooed. The needle is carried as a unit in a housing which includes means for vibrating the needle.

At the present time, the practice of dipping the needle into an ink or pigment is undesirably time consuming and inefficient. In order to obtain dark, permanent tattoos it is important to use adequate amounts of pigment on the points of the tattoo needle. In the process of dipping the needle into the pigment, if the needle is not dipped sufficiently frequently, a pale, poorly visible tattoo will result. Frequent dipping is time consuming and there is the ever-present danger of the needle striking a hard object and being damaged when dipped into the ink supply. In addition to the economic loss when the needle is damaged, the damaged needle, if used, will cause pain while tattooing. The damaged point may also macerate the skin tissue and produce local trauma which activates white blood cells (phagocytes) The phagocytes engulf the pigment particles and carry them away from the tattoo site and this results in fading of the tattoo as well as edema, inflammation, swelling and bleeding at the tattoo site.

Some tattooing apparatus is known which uses a reservoir of ink or pigment to supply the needle with pigment without dipping. However such apparatus cannot regulate pigment flow and the pigment constantly runs out of the reservoir and covers the entire tattoo site as well as the tattooist. This makes it difficult to see the tattoo site and the excess pigment must be cleaned away, thus wasting time and pigment.

The present invention solves this problem by providing a novel arrangement for coupling a source of tattooing ink directly to the tattoo needle unit whereby ink is constantly and controllably available and present on the needle unit as the tattooing operation is performed.

DESCRIPTION OF THE INVENTION

Figure 1:
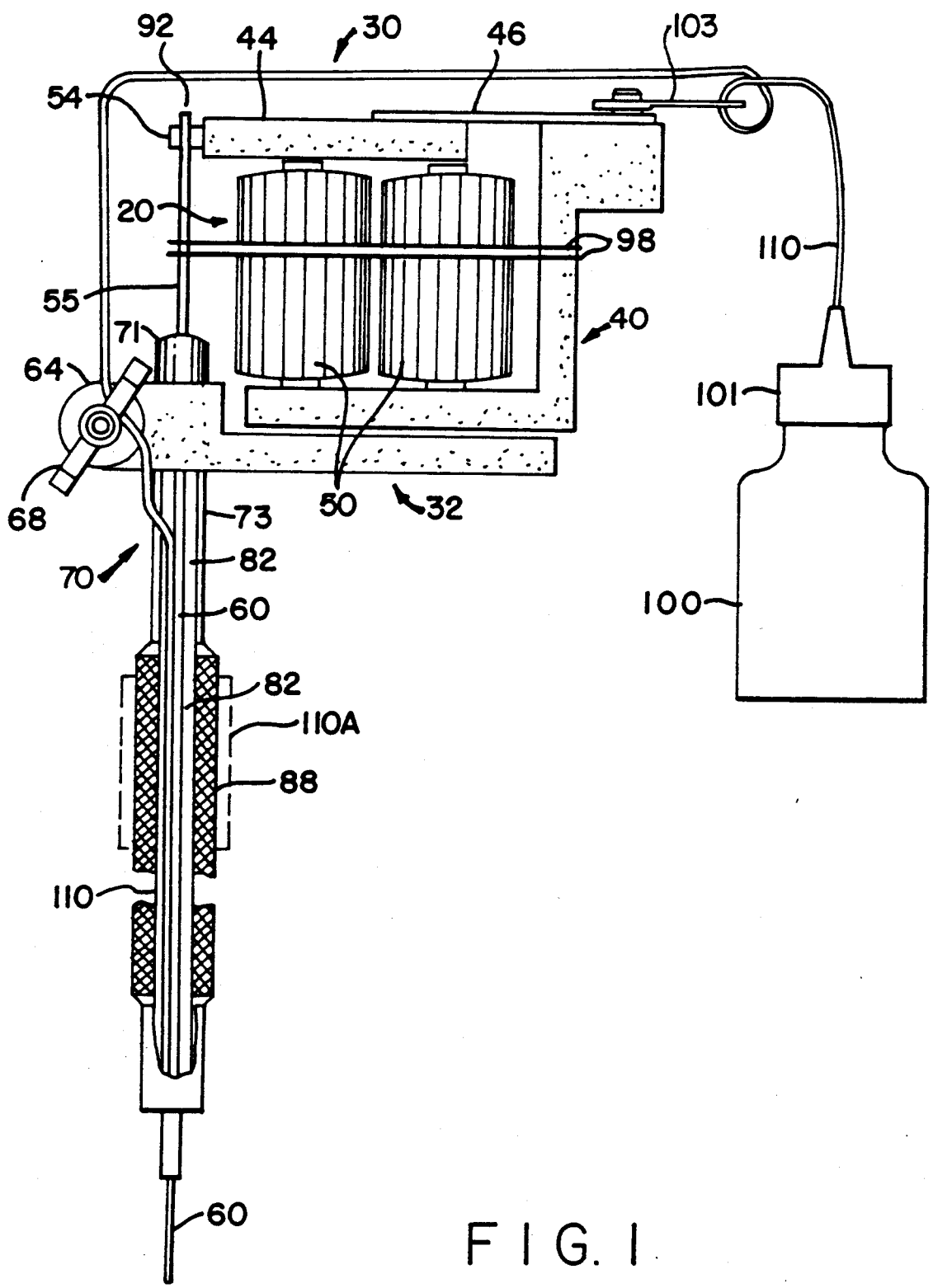
FIG. 1 is a side elevational view of apparatus embodying the invention.
Figure 2:
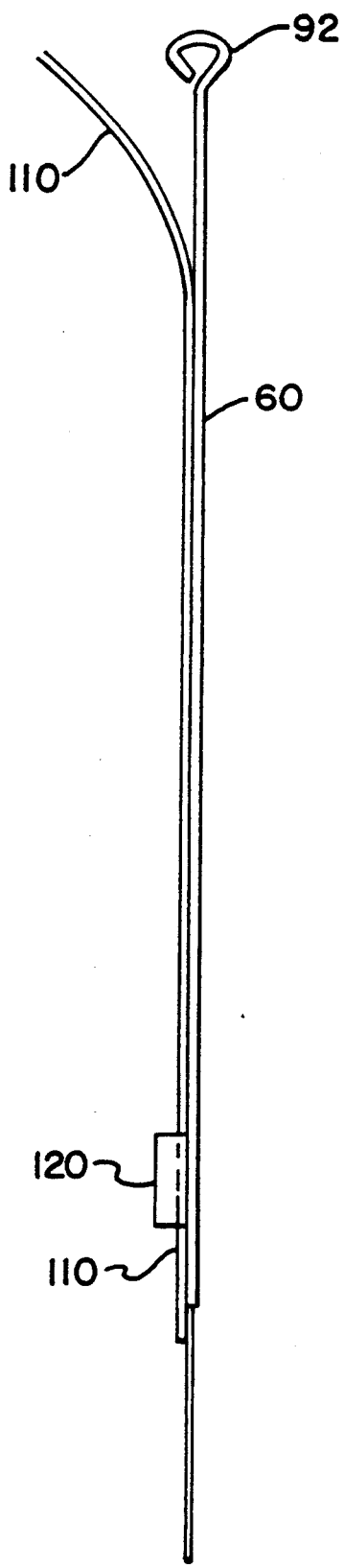
FIG. 2 is an elevational view of a needle used with the holder of FIG. 1.

The principles of the present invention may be used with substantially any type of tattooing machine however it is described herein in connection with a tattoo machine and needle assembly described and claimed in U.S. Pat. No. 4,771,660 which is incorporated herein by reference. Since all of the features of a working tattooing apparatus are shown in that patent, they will not all be shown and described herein.

The needle and needle-holder asssembly 10 used in practicing the invention and shown in the above-identified patent includes a vibrator made up of a U-shaped housing 20 including an upper leg 30, a lower leg 32 and a connecting leg 40. The upper leg is made up of a rigid armature bar 44 and a rearwardly projecting spring-like metal strip 46 which secures the bar 44 to the side leg 40. Electrical coils 50 are mounted on the housing 20 for use in causing the upper arm 30 to vibrate.

The leading end of the upper leg 30 and the front vertical surface of bar 44 carry a projecting pin 54 for coupling a tattooing needle 60 thereto by its ring or eye 92. The leading end of the lower leg 32 is formed with a horizontally disposed split ring 64 which is adapted to receive a needle holder 70 and carries a threaded wing nut 68 for securing the needle holder therein.

The needle holder 70 comprises a hollow metal tube 73 having a longitudinal slot 82 in its wall extending from the upper end 71 of the tube to near the lower end. A tattooing needle 90 is seated in the slot 82 in tube 73 and is accessible at the lower end thereof.

The tattooing apparatus 10 described above is operated in conjunction with a pigment container 100 having a threaded top and suitably positioned. The pigment tube contains the desired pigment, medication or other desired substance. A length of flexible tubing 110 is inserted in a tiny hole in the cap 101 and is secured thereto by means of polyethylene tape. The tube 110 extends from the pigment bottle 100, looped through an apertured connector 103 and then lead alongside the needle shaft 60 and its remote end is secured to the tattoo needle near the lower operating end thereof.

The looping of the tubing 110 through the connector 103 prevents the tubing from being accidentally pulled away from the tattooing apparatus and it also keeps the tubing out of the way of the tattooer.

As the tubing is directed from container 100, it may be threaded over the wing nut 68 or a suitable bracket may be provided on the wing nut shaft holder to guide the tubing.

Figure 3:
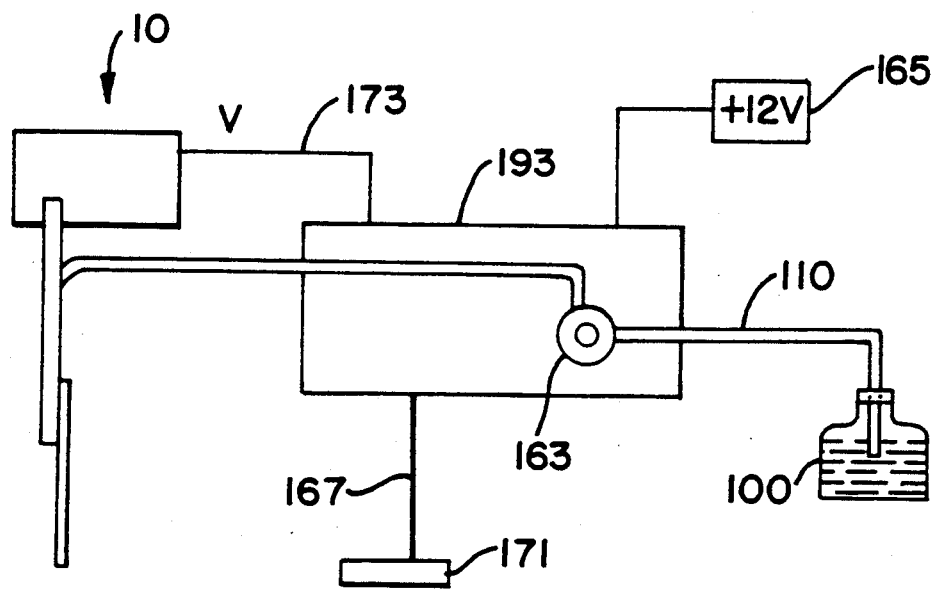
FIG. 3 is a schematic representation of apparatus embodying the invention.
Figure 4:
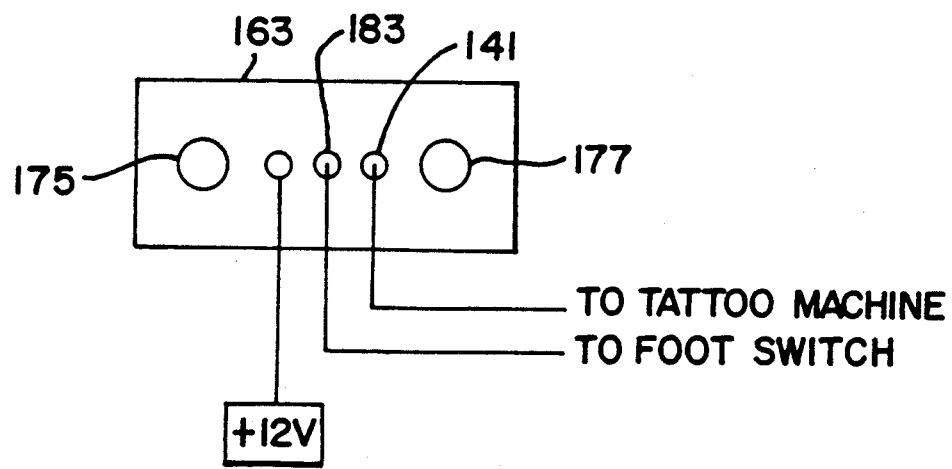
FIG. 4 is a rear view of a portion of the apparatus of FIG. 3.

According to the invention, the flow of pigment from container 100 is controlled by means of a small peristaltic metering pump 163 as illustrated in FIGS. 3 and 4. The apparatus shown in FIGS. 3 and 4 includes a housing 123 which contains the electronics used in the system and pump 163 is a micro-peristaltic pump. The source of pigment or medication 100 which may be sterile is connected by tubing 110 to the pump 163 and to a crimped tube 120 which is secured to the tattooing needle and holds the tubing 110 in place thereat.

The electronic aapparatus in the housing 193 includes means for having a 12 volt power supply 165 connected thereto and with a connection 167 to a foot pedal 171 for turning the pump off and on. A connection 173 is also provided for coupling power to the tattooing apparatus 10.

The housing 163 also includes, referring to FIG. 4, a rheostat 175 for controlling voltage applied to the pump 163 and a rheostat 177 for controlling voltage applied to the tattooing apparatus 10. Connections 181 and 183 for the leads to the foot switch and tattooing machine are also provided on the rear of the housing.

With the arrangement described, the rate of feed of pigment or medication is finely and precisely controlled by the rheostat 175. In addition, the pump rheostat 175 can be used to turn off the power to the pump whereby the tattooing machine can be operated without the pump for a desired period of time.

The system using a pump has the advantage that it approximately doubles tattooing speed and produces darker, easily legible tattoos. The apparatus also reduces needle damage and it reduces tissue build up between the needle points. It also permits the operator to provide fresh pigment for each animal and reduces pigment wastage. It also keeps pigment free of contamination.

It is noted that the vibratory motion of the tattooing needle as it is being operated agitates the tubing 110 which carries pigment thereto and thereby facilitates the movement of pigment toward the tip of the tattoo needle. This motion also constantly mixes the pigment in the tubing and prevents clogging of the tubing.

I claim:

1. A tattooing apparatus comprising
   a tattooing needle having an operating end adapted to penetrate the skin of a subject,
   a source of tattooing pigment,
   a flexible tube having a first end and a second end, said first end being secured to said source of pigment and said second end being secured to said needle near said operating end thereof whereby tattoing pigment can flow from said source and through said flexible tube to said operating end of said needle; and
   a peristaltic pump coupled to said flexible tube for controlling the flow precisely from said source of pigment to said tattooing needle.

2. The apparatus defined in claim 1 and including control means for controlling the voltage applied to said pump and to said tattooing needle.

3. The apparatus defined in claim 1 wherein said pump is a micro-peristaltic pump.

4. The apparatus defined in claim 1 and including a housing containing said pump and electronics for operating said pump and other apparatus,
   electrical power coupled to said housing,
   an electrical connection from said housing to said tattooing needle,
   a foot pedal connected to said housing and said pump whereby said pump can be operated by foot,
   a rheostat coupled to said housing in the circuit for operating said tattooing needle, and
   a second rheostat coupled to said housing and said pump for controlling the speed of operation of said pump.

5. Tattooing apparatus comprising
   a housing,
   an elongated tattooing needle seated in said housing and having a tattooing end,
   means coupled to said housing for vibrating said housing,
   a source of tattooing pigment, and
   a flexible tubing having one end secured to said source and having its other end secured to said needle near said tattooing end thereof whereby tattooing pigment can flow from said source to said needle where it is injected into the skin.

6. The apparatus defined in claim 5 wherein said tubing extends along said tattooing needle.

7. The apparatus defined in claim 5 wherein said housing includes a longitudinal slot in which said tattooing needle is seated and said source of tattooing pigment comprises a container secured to said housing.

8. The apparatus defined in claim 5 and including means guiding said tubing from said source of tattooing pigment to said slot in which said tubing extends to a point of attachment on said tattooing needle.

* * * * *